(12) United States Patent
Schumacher

(10) Patent No.: US 10,278,791 B2
(45) Date of Patent: May 7, 2019

(54) RETAINER AND METHOD FOR PRODUCTION THEREOF

(71) Applicant: RETAINTECHNOLOGY UG, Cologne (DE)

(72) Inventor: Hildegard Brigitte Schumacher, Cologne (DE)

(73) Assignee: RETAINTECHNOLOGY UG, Cologne (DE)

( * ) Notice: Subject to any disclaimer, the term of this patent is extended or adjusted under 35 U.S.C. 154(b) by 34 days.

(21) Appl. No.: 14/846,893

(22) Filed: Sep. 7, 2015

(65) Prior Publication Data

US 2016/0058527 A1 Mar. 3, 2016

Related U.S. Application Data

(63) Continuation of application No. PCT/EP2014/054703, filed on Mar. 11, 2014.

(30) Foreign Application Priority Data

Mar. 13, 2013 (DE) .......................... 10 2013 204 359

(51) Int. Cl.
*A61C 7/00* (2006.01)
*A61C 7/08* (2006.01)
(Continued)

(52) U.S. Cl.
CPC .............. *A61C 7/002* (2013.01); *A61C 5/007* (2013.01); *A61C 7/08* (2013.01); *A61C 7/20* (2013.01); *A61C 9/004* (2013.01)

(58) Field of Classification Search
CPC ........... A61C 7/08; A61C 5/007; A61C 7/002; A61C 7/20; A61C 9/004
See application file for complete search history.

(56) References Cited

U.S. PATENT DOCUMENTS 4,360,342 A * 11/1982 Salvo ..................... A61C 13/26
433/172
4,433,960 A * 2/1984 Garito ..................... A61C 7/00
433/180
(Continued)

FOREIGN PATENT DOCUMENTS

CN 203226911 U 9/2013
DE 10245008 A1 4/2004
(Continued)

*Primary Examiner* — Nicholas D Lucchesi
(74) *Attorney, Agent, or Firm* — Von Rohrscheidt Patents

(57) ABSTRACT

A retainer cooperating with a plurality of teeth and configured to stabilize the plurality of teeth, the retainer including at least one elongated arc which is shaped overall adapted to a natural curvature of a lower jaw or an upper jaw, wherein the at least one elongated arc is locally adapted individually to a surface contour of respective abutting teeth, wherein the retainer is machined from a sheet metal plate and includes two mutually parallel surfaces, wherein the sheet metal plate is made from a nickel titanium alloy, preferably a nitinol, wherein the retainer contacts a tooth surface in an installed condition of the retainer, wherein a machined surface of the retainer faces the tooth surface in the installed condition of the retainer, and wherein an upper side or a lower side of the retainer corresponds to an original surface plane of the sheet metal plate.

19 Claims, 7 Drawing Sheets

(51) Int. Cl.
*A61C 5/00* (2017.01)
*A61C 7/20* (2006.01)
*A61C 9/00* (2006.01)

(56) References Cited

U.S. PATENT DOCUMENTS

| | | | | |
|---|---|---|---|---|
| 4,516,938 | A | * | 5/1985 | Hall .................. A61C 5/00 433/180 |
| 4,533,320 | A | * | 8/1985 | Piekarsky ............. A61C 5/007 433/10 |
| 4,932,866 | A | * | 6/1990 | Guis ..................... A61C 7/146 433/24 |
| 4,976,614 | A | * | 12/1990 | Tepper .................. A61C 7/00 433/18 |
| 7,708,557 | B2 | * | 5/2010 | Rubbert ................ A61C 5/007 433/172 |
| 2004/0072120 | A1 | | 4/2004 | Lauren |
| 2004/0083611 | A1 | | 5/2004 | Rubbert et al. |
| 2005/0181332 | A1 | | 8/2005 | Sernetz |
| 2008/0057460 | A1 | * | 3/2008 | Hicks .................... A61C 5/007 433/20 |
| 2011/0027743 | A1 | * | 2/2011 | Cinader, Jr. ......... A61C 7/10 433/11 |
| 2014/0302448 | A1 | * | 10/2014 | Cassalia ............... A61C 7/28 433/9 |
| 2016/0302890 | A1 | * | 10/2016 | Hamilton .............. A61C 7/00 |

FOREIGN PATENT DOCUMENTS

DE 202012004419 U1 12/2012
JP 2002177299 6/2002

* cited by examiner

RETAINER AND METHOD FOR PRODUCTION THEREOF

RELATED APPLICATIONS

This application is a continuation of International application PCT/EP2014/054703 filed on Mar. 11, 2014, claiming priority from German patent application DE 10 2013 204 359,7, filed on Mar. 13, 2013 both of which are incorporated in their entirety by this reference.

FIELD OF THE INVENTION

The invention relates to a retainer.

BACKGROUND OF THE INVENTION

Retainers have already been known for some time. They basically serve to fix the tooth position of a patient. That is, by means of a retainer a status quo is fixed with respect to the tooth position in order to prevent possible changes in the tooth position over time.

Particularly typical is the use of retainers in the course of a post-treatment of an orthodontic treatment. The latter involved an active influence on the tooth position of a patient, wherein by means of suitable devices forces are exerted to the teeth, such that they change their position or orientation over time. After such an orthodontic treatment is finished and the use of the respective device is completed the teeth tend to return to their former position. If no post-treatment is performed the result obtained by means of the active treatment will at least partially regress and consequently negate the active treatment.

Therefore, subsequently to the active treatment typically the use of a retainer is recommended which fixes the newly obtained tooth position. In order to achieve this, such retainers are connected to a plurality of teeth, wherein the retainer is adapted to receive forces produced due to a desired intrinsic mobility of a tooth and to distribute the forces to the remaining teeth. Thus, a movement of the tooth is prevented. Such retainers are known for example from DE 20 2012 004 419 U1 and DE 102 45 008 A1, wherein in the latter document a so-called "2-point retainer" is described, which is firmly connected with only two teeth.

In the known retainers it has proven to be particularly disadvantageous that a precise adaption of the respective retainer to the individual contours of the teeth to be fixed on the one hand is very expensive and on the other hand is usually characterized by only low precision even in the case of careful handling by an experienced dental technician. This is mainly due to the production of today's known retainers, which are adapted to the shape of the respective dental impression in a manual process by bending a starting material—typically a metal strand. The precision of such a processing is naturally limited, wherein the finished retainer can have a distance in the order of a few millimeters from a tooth to be fixed. Then, in order to close this "gap" between retainer and tooth it is necessary to provide a correspondingly larger adhesive bond that reliably encloses the retainers despite of its great distance from the tooth and consequently connects the retainer to the teeth in a force-fitting manner. This is disadvantageous both for the wearing comfort of the retainer and its durability, because shear forces occur during chewing and acting on the retainer or its adhesive bond are the greater the more "attack surface" they provide in the oral cavity. This often results in that a retainer is detached locally and then has to be fixed again manually. Likewise, regularly a fracture of the retainer occurs.

Furthermore, the known retainers have the disadvantage that their purely passive effect can already be "activated" by minor accidental dislocations of the retainer. Thus, it regularly happens that a retainer in an interdental area, where it freely, that is unglued, extends from one tooth to the respective adjacent tooth, is accidentally bent, for example as a result of an interacting chewing force.

By bending the projected length of the retainer is locally reduced, which results in that the retainer from then on pulls the adjacent teeth to one another. That is, the retainer is changed by means of the unwanted deformation from a passive to an active element, which now no longer acts as a purely fixing element, but actively influences the tooth position. Such an influence, however, has to be avoided in any case, since the active dental treatment is typically already completed at the time of use of the retainer and further teeth movements are not desirable. If a deformation of a retainer occurs, it may even be necessary to completely replace it.

Another disadvantage of today's retainers is their fixing effect, which can be referred to as "interlocking". This interlocking means that a retainer known in the art in fact achieves the desired stabilizing effect, however, it couples the teeth so strongly to each other, that any load acting locally on a tooth is substantially evenly distributed to all teeth. An independent movement in a sagittal direction is largely suppressed because of the retainer. The same applies to vertical movements and rotations of the teeth about their vertical axis. As a consequence the force impact due to external forces is decreased permanently for each individual tooth which has the consequence that the alveolar bone in which the teeth are anchored by their roots, is much less irritated than is the case without the retainer, i.e. under "natural conditions". This irritation, however, is particularly important because it leads to a stimulation of the bone tissue, so that it will be preserved. If the irritation of the bone tissue is decreased, it degenerates. The decreasing force impact on each individual tooth has accordingly the consequence that the alveolar bone degenerates in the region of the "interlocked" teeth because the impact of external forces on the bone tissue locally decreases.

From the foregoing it is clear that two kinds of tooth movements have to be distinguished: on the one hand tooth migrations occur, which represent a continuous movement of the tooth back to a malposition, wherein said tooth migrations should be suppressed by the retainer. On the other hand teeth also have a certain intrinsic mobility due to which the teeth are movable in all directions within a certain margin (about 0.2 mm) in particular when chewing loads occur, wherein the teeth return to their initial position after the load is relieved. However, these intrinsic movements are extremely important because of the associated stimulation of the bone tissue and should be restricted as little as possible by a retainer.

From EP 1782748 A1 a retainer is known which is made from of a zirconium oxide, i.e. a ceramic material. Due to the fact that the zirconium oxide is not deformable the retainer is milled or ground from a block. Zirconium oxide is characterized by a high flexural strength and is therefore very rigid and unyielding. However, because of the risk of fracture inherent to the brittle ceramic material the known retainer is very thick-walled and voluminous. However, these characteristics of the known retainers result in the above-described disadvantage of "interlocking", which restricts the movement of the teeth in the socket (tooth socket) and become non-physiological, which eventually leads to a degeneration of the bone tissue.

BRIEF SUMMARY OF THE INVENTION

It is an object of the present invention to overcome the drawbacks of the known retainers.

The object is achieved by a retainer cooperating with a plurality of teeth and suitable for stabilizing the teeth, including at least one elongated arc, wherein the arc locally comprises a curved shape following the natural curvature of a lower jaw or an upper jaw and is locally individually adapted to a surface contour of a respective abutting tooth, wherein the retainer is made of a metal and is machined from a plate-shaped part, in particular a sheet, of the metal which comprises two mutually parallel surfaces.

Furthermore, the object is achieved by a method of manufacturing an above-mentioned retainer, the method including the steps:

a) a contour of teeth individually to be stabilized is detected.

b) the retainer is machined from a metal sheet.

Herein, the term "contour" of the teeth quasi means their topography. This means that the detection of the contour of the teeth includes the detection of the tooth surface which is to cooperate with the retainer such that the treating physician is provided with information indicating which shape the retainer should have both globally and locally in order to abut the teeth as closely as possible.

With respect to the retainer described above the aforementioned object is achieved according to the invention in that the metal is formed from a nickel titanium alloy, more preferably from a nitinol and a machined surface of the retainer in its installed state faces a tooth surface which the retainer abuts, and an upper surface or a lower surface of the retainer corresponds to an original metal sheet plane. Nickel titanium alloys and nitinol are shape memory materials that are particularly well suited for the retainer according to the invention, since they have a so-called "pseudo-elastic" material behavior (also called "super elasticity"). This material behavior means with respect to the present invention that the retainer can even experience relatively large deflections without thereby being deformed plastically—i.e. permanently. The elastic region of the shape memory material is formed unusually large due to a phase transformation within the material under the influence of tension and can exceed twenty times the elastic region of a "normal" steel, such as is commonly used for today's retainers. This leads to the particular advantage that such a retainer according to the invention practically cannot be deformed plastically, which means that a "kink" or another accidental permanent deformation of the retainer is not possible. Thus, it is not possible that the retainer according to the invention is accidentally "activated" due to a local deflection of a single tooth as a result of its intrinsic mobility (for example under the impact of high local chewing forces caused e.g. by biting on a grain). As a result a movement of the teeth caused by the retainer comparable to an orthodontic treatment is excluded with the use of the retainer according to the invention.

Furthermore, the shape memory material is advantageous in terms of the above-described problems with respect to the lacking stimulation of the alveolar bone. This is because short-term positional changes of the teeth, which are based on local forces acting on individual teeth—i.e. as a part of their intrinsic mobility—are enabled due to the pseudo-elasticity of the material, i.e. extremely low elastic restoring forces. By means of a reversible, elastic deformation of the retainer the applied force is yielded and the tooth can be deflected in a natural amount within the socket, that is in the tooth socket, where the tooth is suspended by collagen fibers. Once the force impact is no longer present, both the retainer and the affected tooth return to their original shape or position.

The pseudo elasticity of the shape memory material, moreover, promotes the durability of the retainer according to the invention. Thus, it is not subject to the risk of a deformation induced fracture or a "fatigue" of the restoring properties.

In addition, the shape memory material is relatively soft due to the low modulus of elasticity, so that it can be easier deformed elastically. Thus, a breakage of a junction to a tooth is less likely to occur than with retainers of the prior art. Furthermore, the low stiffness is positive in view of the possibility of a sagittal and vertical deformation of the individual teeth, since the retainer couples or interlocks the connected teeth less stiffly.

Accordingly, a retainer formed from a shape memory material is also preferable with respect to a lower interlocking effect.

Through the use of nickel titanium alloys, in particular nitinol, a previously existing conflict of interest in the use and formation of retainers is solved: on the one hand, one strives to connect the teeth to one another in a force transmitting manner in order to counteract unwanted tooth movements and tooth migrations. On the other hand the physiological intrinsic mobility of the individual teeth should be restricted as little as possible. Both are possible with the method or the retainer according to the invention, however, not with the retainers previously known. This is the case, because nickel titanium alloys, in particular nitinol, are characterized in that with rapidly occurring loads an (elastic) deformation can take place and with slowly occurring loads no deformation of the retainer is caused. This is particularly advantageous because in chewing movements the desired shortly occurring movements of the teeth are permitted in the frame of their intrinsic mobility while continuous movements of the teeth or tooth migration towards a malposition are being suppressed. Even if deflections are permitted, there is always a small restoring force towards the initial position of the retainer. Steel, for example, has a certain restoring force, but this is significantly lower and there is a high probability that the steel will be permanently bent and thus will exert no restoring force at all, but on the contrary exerts a force on the teeth, which directs them into a malposition.

Regarding the feature of the retainer according to the invention that a machined surface of the retainer in its installed state faces a tooth surface which the retainer abuts and an upper surface or a lower surface of the retainer corresponds to the original plane of the metal sheet, this is advantageous because in this way a bending free separation of the retainer is possible or takes place. This means that the retainer is produced in the form in which it eventually abuts the teeth of a patient. A bending of the metal sheet for producing the retainer is not possible at all for a material with super elastic properties, because no permanent deformations can be made. The retainer according to the invention thus is a finished product that can be used without further processing. An advantageous finishing process in the form of electro-polishing is not considered at this point.

In a retainer according to the invention, which is connected in bonding portions by means of a bonding material to the respective adjacent teeth in a force-transmitting manner, and preferably is embedded in a bonding material adherent to the respective tooth, it is also particularly advantageous when in each of the bonding portions a maximum distance between a respective tooth surface and a position of the retainer, which measured perpendicular to the respective tooth surface has the smallest distance to this tooth surface, is at most 0.1 mm, preferably at most 0.01 mm, more preferably at most 0.005 mm. Such a retainer is adapted particularly precisely to the natural contour of the respective teeth. This is advantageous in that the insertion of such a retainer is particularly easy for the treating specialist, since the retainer practically exactly abuts the teeth only in a single position. Therefore, an accidental "oblique" installation is almost impossible. In addition, the exact adaptation in accordance with the above explanation promotes the use of thin bonding portions, which in turn has a positive effect on the durability and susceptibility to failures of the retainer. Moreover, a thin layer of the bonding material is perceived as less disturbing by the patient.

Advantageously, the retainer is locally formed so as to protrude at least partially into at least one interdental space between two adjacent teeth so that a relative motion between the retainer and the teeth in a longitudinal direction of the retainer is blocked even if the retainer abuts the teeth in an unconnected state.

Here, the term "unconnected state" means that the retainer is not yet connected to the teeth in a force-transferring manner and consequently, for example, could be manually removed from the oral cavity again. On the contrary, in a "connected state" the retainer is connected fixedly with the teeth, in particular bonded. The described shaping of the retainer is exclusively possible by means of the method according to the invention. A formation of regions that protrude into the interdental spaces is inconceivable by means of the usual prior art deformation methods.

The shaping of the retainer in the manner described provides a number of advantages. For this purpose, reference is made to the above-described problem of "interlocking". This arises from the fact that today's usual retainers couple the teeth strongly to each other, so that an independent intrinsic motion of the teeth is restricted very strongly. The accompanying problem of a degeneration of the alveolar bone has already been described above. Through the guidance of the retainer up into the interdental spaces now the effect is achieved, that the so-called "free length", that is the length over which the retainer abuts freely, i.e. "unbonded" at the teeth between two adjacent teeth, is considerably greater in the retainer according to the invention than in known retainers. In the latter, the retainer extends essentially straight between two adjacent junctions, i.e. over the shortest possible path. In the retainer according to the invention, however, the retainer extends in a kind of "detour" as the retainer is guided up into the interdental spaces. This has the consequence that a "built-in length" of the retainer according to the invention, i.e. an unwound length thereof, is significantly longer than the unwound length of a conventional retainer. Here again the pseudo-elastic behavior of the nickel-titanium alloy or the nitinol comes into effect, because only if a pseudo-elastic material is used a noticeable increase in the deflection ability can be achieved due to an increase of the per se short distance between two teeth. By means of the increased length between two adhesive bonds the flexibility of the retainer is further increased. If, however, a rigid material such as ceramic is used for a retainer, this may indeed also be designed such that it protrudes into the interdental spaces of adjacent teeth, however, the flexibility or elasticity of the retainer is not increased, but rather due to the rigidity of the ceramic material still no sufficient intrinsic movements of the teeth are enabled.

The increased free length between two junctions eventually has the advantageous effect of reducing the described interlocking of the teeth as compared to what is known in the art. This is due to the fact that the coupling of a respective tooth to the respective adjacent tooth is the less the longer the bonding portion is, which couples both teeth to each other. This greater freedom of movement manifests itself in practice in that the individual teeth can move significantly more freely both in the sagittal and in the transverse and vertical directions when using the retainer according to the invention clearly than in use of a conventional retainer. In addition, the tooth is able to rotate and to change its axial inclination. Thus, the previously disadvantageous lack of a stimulation of the alveolar bone is substantially eliminated. Nevertheless, the coupling effect of the teeth in the transverse direction, i.e. the coupling, which in principle is to be achieved by means of the retainer, is not adversely affected by the greater free length of the retainer according to the invention.

The greater free length of the retainer according to the invention is also advantageous for its durability. Thus, in the retainer according to the invention fractures of the arc or the respective junction occur relative rarely. This is because the arc can be more easily deformed freely than in retainers according to the prior art. In the latter deformations have to be reduced over short distances, wherein the deflections sometimes result in a fracture of the retainer or a fracture of the adjacent junction.

Furthermore, the high accuracy of fit which is demonstrated here by the adaptation of the retainer up into the interdental spaces, is basically advantageous for the wearing comfort of the retainer. Here, reference is made to the above statements.

In an advantageous embodiment of the retainer the arc has locally a radius of curvature of 1.0 mm or less, preferably 0.5 mm or less, more preferably 0.2 mm or less. Such a small radius of curvature is provided for example in the region of an interdental space. At such a point the arc of the retainer extends locally quasi towards a "tip". In addition, such "sharp" curvatures in the arc may be adapted to locally replicate topographies present at the tooth surfaces. A formation of such bending radii is inconceivable with conventional retainers.

The retainer according to the invention is particularly advantageous when the arc comprises a parallelogram shaped, preferably a square cross section, wherein the side lengths of the cross section are at most 0.7 mm, preferably at most 0.5 mm, more preferably at most 0.3 mm. A square cross section is particularly suitable. An "edge-shaped" configuration of the retainer primarily offers the advantage of a so-called "torque control", i.e. of stabilizing the inclination or the axial inclination of the teeth. This is due to the fact that the edge-shaped retainer can appropriately interlock with the bonding material of the junction and thus prevents it from the respective rotational movement. Usual retainers on the other hand have a round or oval cross section, by means of which such a stabilization due to lack of interlocking of the cross section of the retainer with the respective adhesive bond is not obtained.

The small cross sectional size of the retainer according to the invention moreover results in that the junctions with the tooth surface can be made relative shallow. This on the one hand promotes the durability of the retainer because an attack surface for shear forces can be minimized and on the other hand the wearing comfort since the patient only feels a little unevenness on the tooth surfaces.

Preferably, the retainer according to the invention is used as a so-called "6-point retainer" and as such is connected to more than two teeth or more than three teeth in a force-transmitting manner. However, a use as a so-called "2-point retainer" is conceivable in principle.

With regard to the connection of the retainer to the teeth it is particularly advantageous if the retainer is fully enclosed by the bonding material at the bonding portions. This means that the retainer is surrounded by the bonding material at the bonding portions at four sides. Thus, the retainer is at least in portions completely embedded within the plastic mass, so that in the corresponding portion no part of the retainer is exposed or visible. In this way, a particularly permanent connection between the retainer and the tooth is provided.

In a particularly advantageous embodiment the retainer is made in one piece. This is the normal case in use of the method according to the invention, because in the course of preparing the retainer from the metal sheet a single continuous piece is obtained, which forms the complete retainer. Nevertheless, it is conceivable to assemble the retainer according to the invention from a plurality of individual parts.

If one regards the retainer according to the invention as enclosed by a fictive inner enveloping parabola and a fictive outer enveloping parabola seen in the plan view, wherein the inner enveloping parabola abuts the innermost points of the retainer and the outer enveloping parabola abuts the outermost points of the retainer, then such a retainer is preferable, in which locally in the region of an interdental space a maximum distance between the inner enveloping parabola and the outer enveloping parabola measured perpendicular to the inner enveloping parabola is at least 1.0 mm, preferably 1.5 mm, more preferably 2.0 mm. This distance between the enveloping parabolas is conceivable as a measure of the "penetration depth" of the retainer into the interdental spaces. The further the retainer follows these interdental spaces, the more precisely it rests on the teeth and the longer is the free length between adjacent junctions. In this regard, a retainer comprising the distances described is particularly advantageous.

Further, it may be advantageous when the retainer at least partially has a roughened surface, wherein preferably all surfaces (lower surface, upper surface, front surface, back surface) of the retainer are roughened. Such roughening enables a better bond between the retainer and the material by means of which the retainer is connected to the teeth.

In an advantageous embodiment the retainer is treated by electro-polishing or plasma polishing. The advantages of such retainers have already been explained above.

Finally, it is particularly advantageous if the nickel titanium alloy has an AF temperature between 25° C. and 35° C., preferably between 27° C. and 33° C., more preferably between 29° C. and 31° C. It has been found that the closer the AF temperature is at the temperature at which the workpiece is used, which in the case of retainers corresponds to the body temperature of about 37° C. the more reliable the desired region of the stress-induced martensite plateau is reached in elongation of the material.

According to the invention the underlying object is achieved starting from a method of the type described above by the following method steps:

c) the detected contour of the teeth is converted in a preferably digital model and the retainer is designed on the basis of the model.

d) the designed retainer is machined from the metal sheet, which is made from of a nickel titanium alloy, preferably of nitinol, on the basis of the model by means of a computer-controlled process, wherein a machining surface of the retainer in its installed state faces to a tooth surface which the retainer abuts, and an upper surface or a lower surface of the retainer corresponds to an original metal sheet plane.

The invention is based on the idea that an improvement of the precision in the adaptation of the retainer to the respective teeth contours of the patient results in a considerable improvement of both the effect of the retainer and the wearing comfort. Furthermore, accidental treatment errors that are based on an accidental activation of a retainer, can be avoided.

The method according to the invention enables a significant increase in the precision of the finished retainer over known today's retainers in a way that locally a distance of the retainer from the respective tooth surface, which it is to abut, is very low. From the detected contour a particularly precise model for a retainer can be obtained by the use of a computer with a corresponding CAD (Computer Aided Design) software. Based on this model by means of a computer-controlled machining process (Computer Aided Manufacturing—CAM) finally the retainer can be worked out automatically from the metal sheet in the exact shape specified by the CAD model. This procedure is therefore also referred to as "CAD-CAM method". Since the retainer according to the invention is worked out from the metal sheet, this method is a so-called subtractive method.

As a result, the method according to the invention produces a retainer which exactly abuts the contour of the detected teeth and has a secure fit. In particular, a subsequent deformation or processing of the retainer—whether by machine or by hand—is not necessary and, when using a nickel titanium alloy, in particular nitinol, with its pseudo-elastic properties, even impossible, because the material after an imposed deformation returns into its initial position. The retainer according to the invention, thus, once it has been worked out from the metal sheet, obtains directly its eventual shape (both globally and locally), wherein no further adaptations are necessary or possible. This results in several advantages:

The junctions at which the retainer is to be connected to the respective tooth, can be implemented much shallower than is the case according to the prior art. That is, a layer thickness of the required plastic material which forms the junction, is smaller.

This is due to the fact that the retainer abuts very closely or directly at the corresponding tooth surface. The plastic layer, by means of which such retainers are typically connected to the teeth, is required to have a comparatively small extension in a direction perpendicular to the tooth surface in order to fully enclose or embed or encase the retainer. A bridging of free spaces between the retainer and the tooth, as is regularly required in the prior art, is not necessary. A "shallow" junction on the one hand considerably improves the wearing comfort of such a retainer. This primarily concerns a more pleasant wearing comfort, since the spatial extension of the foreign body, which the retainer with the bonding material ultimately represents in the patient's mouth, is very small. In addition, it facilitates the patient's oral hygiene. On the other hand a thin junction due to its small dimensions within the oral cavity has a significantly smaller surface than is the case with junctions according to the prior art, and is therefore subjected to significantly lower shear forces or chewing forces. The latter is particularly advantageous for the durability of a retainer produced by means of the method according to the invention, since the probability of detachment of the retainer from one or more teeth due to such force impacts is significantly reduced. In view of the durability of the retainer it is also advantageous that by means of the pseudo elasticity of the nickel titanium alloy or the nitinol at a force impact by mastication and a resultant tooth deflection less stress, i.e. tension, is produced in the retainer tooth composite, which in the worst case could lead to stress fracture.

The lack of plastic deformability of a retainer formed from a shape memory material is also the reason why such retainers are not yet available on the market. Thus, the currently known production processes, which—as described—require an individual molding of the retainer with respect to the respective row of teeth to be fixed by bending, are not adapted or cannot be used to form such a retainer from a nickel titanium alloy, because it cannot be deformed permanently or plastically. Only by means of the method according to the invention—i.e. by working out the retainer from a metal sheet in accordance with the specified orientation—the use of a shape memory material is conceivable at all.

Another important advantage of a precisely shaped retainer is its simplicity in terms of its application or introduction in a patient. In retainers according to the prior art, the treating physician is quickly tempted to apply points of the retainer, at which a distance between the same and the tooth to be fixed is relatively large, manually and subsequently to bond. During this application the retainer is elastically deformed and accordingly develops to a restoring force, which tends to move it back into its previous position. By fixing the retainer to the tooth this restoring force is preserved and acts from now on onto the respective tooth. This means that the retainer acts no longer as a purely passive element which merely fixes the teeth in their current position, but is activated and causes a movement of the respective tooth because of the force. By means of the production process of the invention the retainer is, however, precisely adapted to the teeth such that such an accidental activation of the same is almost impossible and in particular not necessary. Consequently, by the method the later success of treatment can be significantly improved and the use of a retainer is significantly safer than in the prior art.

The retainer is worked out from the metal sheet in such a way, that a machining surface of the retainer in an installed state thereof faces to a tooth surface at which the retainer abuts and which is adapted to the respective surface contours of the respective teeth and an upper surface or a lower surface of the retainer corresponds to an original metal sheet plane. An "upper surface" and a "lower surface" of the retainer mean those surfaces thereof that are aligned parallel to one another. In the example of FIG. 1 of the exemplary embodiments the upper surface of the retainer is the surface that is visible to the viewer of the figure. The "machining surface" means the surface of the retainer, which is obtained through working out the retainer from the metal sheet. Thus, the machining surface is that plane, which is arranged perpendicular to the plane of FIG. 1 of the exemplary embodiments. The machining surface typically abuts the surface of the respective teeth to be fixed. This machining surface at least partially abuts the tooth surface. The opposite plane facing away from the tooth surface can equally be interpreted as a machining surface.

This orientation during working out the retainer from the metal sheet enables to produce the same directly in the shape in which it will later be applied to the teeth of the respective patient. In particular, the curved path which globally viewed is approximately parabolic, can be "traversed" directly automated by means of an appropriate tool, so that the retainer can be separated without bending or deformation of the material. From the above mentioned DE 102 45 008 A1 basically also a method for working out a retainer from a metal sheet can be extracted, wherein reference is made to the exemplary embodiment according to FIG. 4 of said document. However, in the retainer described therein the machining surface also called as processing plane coincides with the upper surface and the lower surface, respectively, of the retainer. The worked out retainer therefore as a result is "flat" (which due to the significantly increased adhesive end portions is required) and has to be adapted in a further step to the teeth, wherein it is typically bent. Such an additional step, which is typically carried out manually, in turn carries the risk of inaccuracy regarding the fit of the retainer and is not necessary by means of the method according to the invention and due to the characteristics of the nickel titanium alloy even not possible.

The method according to the invention is particularly advantageous if the retainer is cut out from the metal sheet by laser cutting or by wire erosion, wherein by use of this method the cutting out is carried out by the impact of heat and not by a shearing process of two cutting edges moving past each other. Such cutting methods are particularly accurate. Furthermore, associated devices which are adapted for cutting metal sheets in an automated manner are readily available. Alternatively, however, other methods are conceivable, for example, water-jet cutting.

The method is also particularly advantageous if the contour of the teeth to be stabilized is detected intraorally. This is enabled by means of so-called "intraoral scanners". In the meantime, conventional moulding processes, in which an impression (negative) of the teeth be stabilized is made by means of an impression material and a positive is obtained by casting the impression with a plaster material, are of particular high quality. Nevertheless, the precision of intraoral scans is better process related, since even when using good impression materials always a drying-induced shrinkage takes place and during the transfer of the contour information of the natural tooth to the impression template and in turn from the template to the finished form inevitably a loss occurs. In addition, regularly bubbles by entrapped air occur during the impression process which has a negative effect on the precision of the positive. In today's usual retainers this is irrelevant since their precision cannot detect such small discrepancies between the model and the real tooth. In retainers which are produced by means of the method according to the invention the intraoral scan, however, can provide an advantage in the final result of the retainer.

In a particularly advantageous embodiment of the method according to the invention the metal sheet from which the retainer is worked out, is made up of a pre-curved metal sheet, wherein a curvature axis about which the metal sheet is at least curved in an unbent state of the metal sheet extends in a metal sheet plane. A pre-curved metal sheet during the production process offers the opportunity to produce the retainers likewise curved.

By use of a plane metal sheet the retainer produced according to the invention has an arc shape, wherein the retainer, however, has two planes extending parallel to each other. Consequently, the retainer worked out from a plan metal sheet could be laid flat on a plane surface, such as a tabletop, wherein a lower surface of the retainer would form a full-surface contact with the tabletop. By means of the use of pre-curved metal sheets from which the retainer is worked out, the retainer obtains an additional (vertical) dimension, because as a consequence it also has a curved geometry. Using the example of the tabletop this would mean that the retainer would only rest on the plane tabletop with its lower surface in portions and otherwise would be raised from the tabletop. Such an option to form the retainer with an additional dimension possibly allows a better adaptation of the retainer to the global shape of the dental arc.

In a particularly advantageous method the retainer is electro-polished or plasma polished after it has been cut out from the sheet, whereby edges are rounded. Such a treatment of the retainer reduces the micro-roughness and the nano-roughness of its surface and thus impedes sticking of potentially harmful germs. Further, the corrosion resistance of the retainer is increased. The upper surface and the lower surface newly formed after polishing according to the present invention are likewise to be understood as an "original metal sheet plane" according to the independent method claim, since the removal of the material by polishing is only small, in particular since the removal of material occurs in the micrometer range.

BRIEF DESCRIPTION OF THE DRAWINGS

Hereinafter, the invention described above is explained in detail with reference to an exemplary embodiment illustrated in drawing figures, wherein.

DETAILED DESCRIPTION OF THE INVENTION

Figure 1:
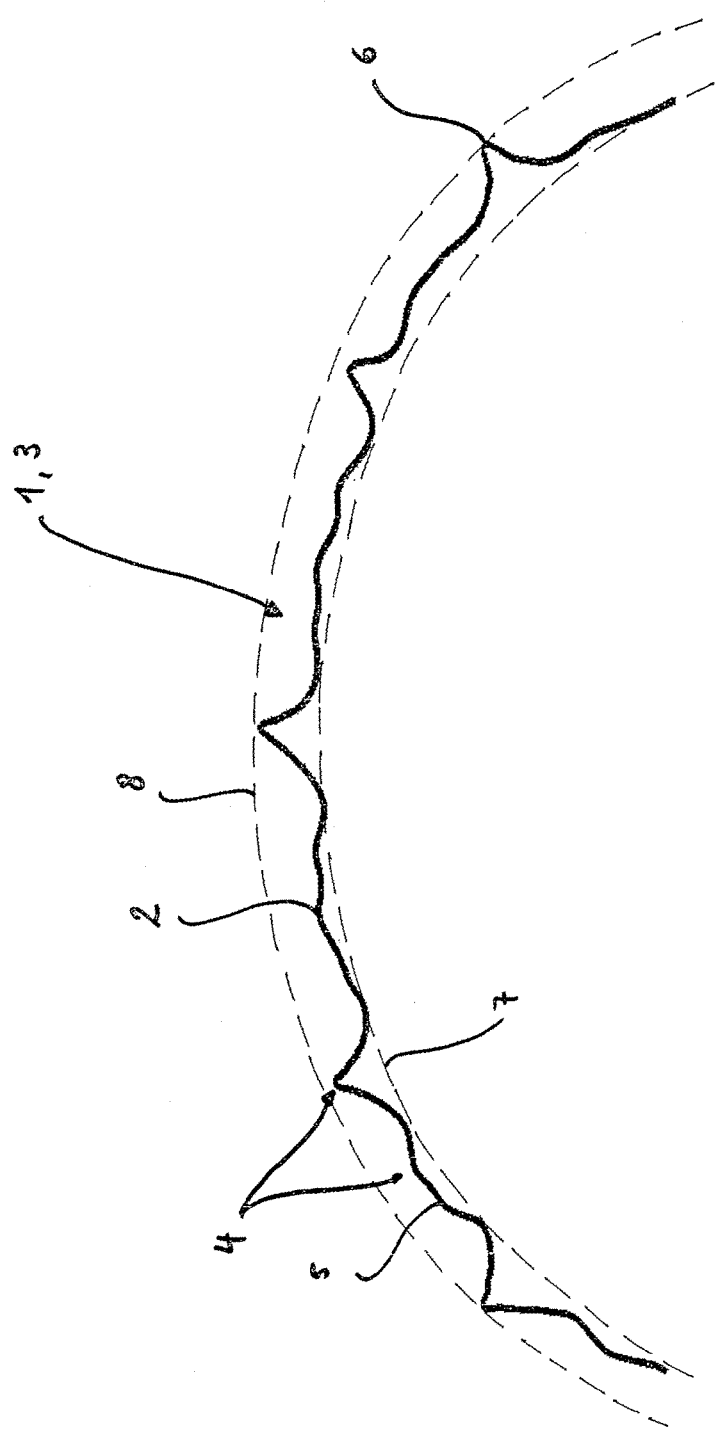
FIG. 1 is a plan view of a retainer according to the invention for use in the upper jaw.

A first exemplary embodiment, shown in FIG. 1, includes a retainer 1, which is adapted for use in a upper jaw. The retainer 1 is configured as a 6-point retainer and is connected to six teeth in a force-transmitting manner after it has been inserted into the respective patient. The retainer 1 is shown in FIG. 1 in a plan view, so that an upper surface 2 of the retainer 1 is visible.

The retainer 1 includes an arc 3, the global shape of which is parabolic. This global shape of the arc 3 is determined by the shape of the respective upper jaw, into which the retainer 1 is to be inserted. The arc 3 includes locally individual formations 4, which can be divided into two categories. The first category refers to formations 4 in the form of "shallow waves" 5 which are configured to adapt the retainer 1 to an individual topography of the adjacent teeth. These shallow waves 5 are therefore correspondingly adapted to an individual tooth shape of a patient. The second category describes "tips" 6 which form the points of the arc 3, which enter into interdental spaces between adjacent teeth. In the tips 6 the arc 3 has small radii of curvature, which are here in the range of 0.5 mm to 1.0 mm. These tips 6 are different from the waves 5 by means of their amplitudes relative to the global shape of the arc 3.

This can be shown on the basis of two enveloping parabolas 7, 8 enclosing the arc 3 and shown in dashed lines in FIG. 1. These enveloping parabolas 7, 8 describe an inner boundary line and an outer boundary line of the retainer 1, wherein the inner enveloping parabola 7 includes those points that are located innermost relative to the shape of the retainer 1 and the outer enveloping parabola includes those points that are located outermost relative to the shape of the retainer 1. Thus, the outer enveloping parabola 8 extends substantially through maximum points of the tips 6. In the example shown a distance as measured perpendicular to the enveloping parabola 7 between the same and the outer enveloping parabola 8 is continuously about 2 mm. This value describes at the same time the above-mentioned amplitude of the tips 6. A parabola which would be laid substantially through maximum points of the shallow waves 5 would have a much smaller distance from the inner enveloping parabola 7. That is, the amplitude of the waves 5 in comparison to the tips 6 is small. This is clearly visible in the form of the retainer 1 shown.

The retainer 1 is formed from the material nitinol and was cut out from a corresponding nitinol sheet by a laser cutting process. Prior to this step it is always necessary to detect the respective contour to be reproduced of teeth to be stabilized. This is typically implemented by the scan of an impression that reproduces a dental impression of the upper jaw or lower jaw, or by means of a so-called "intraoral scan" which is made by means of an intraoral scanner. In the latter method, the shape of the teeth is detected directly in the patient's mouth. Here, it is advantageous that this method is possible comparatively quickly and allows greater precision than an impression process.

The result of the respective scan of the teeth is then processed by means of a CAD software and a three-dimensional model of the retainer 1 is created, which is adapted very well to the scan and consequently to the real topography of the respective teeth. Based on the model subsequently the laser is programmed, by means of which the retainer 1 is cut out. This process step is also referred to as computer aided manufacturing (CAM).

Figure 2:
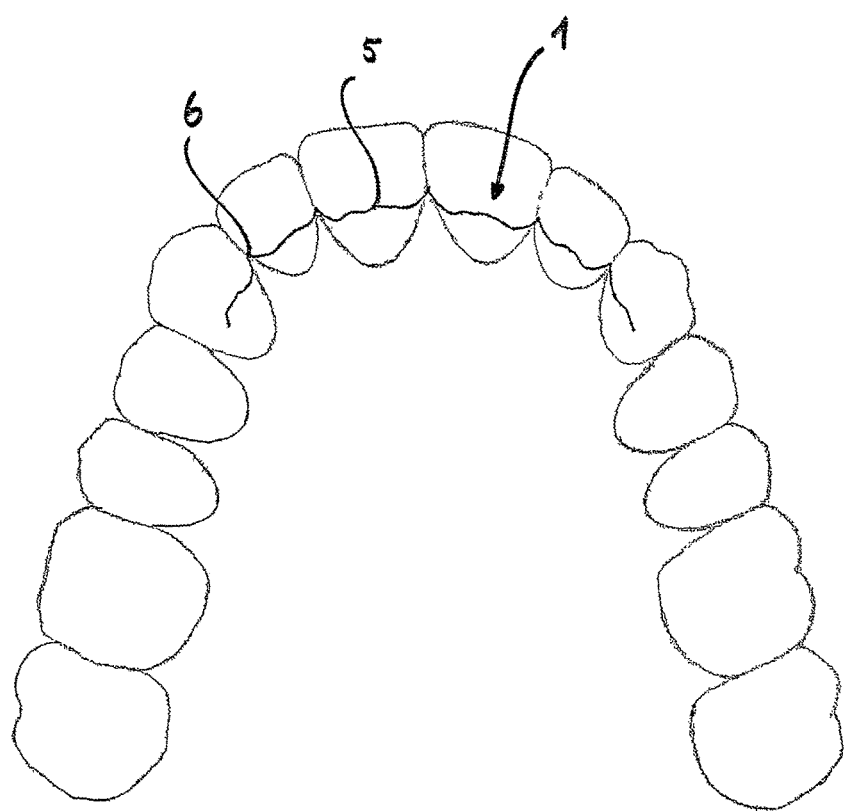
FIG. 2 is similar to FIG. 1, but is used on a model of the upper jaw.

The retainer 1 is shown in FIG. 2 in an inserted state in which the retainer 1 is initially loosely applied to the teeth. The retainer 1 is formed such that a distance between a tooth surface at which the retainer 1 abuts and a point of the retainer 1, the distance of which measured perpendicular to the tooth surface is the smallest, is at most 10 μm. i.e. 0.01 mm. Such a precision cannot be realized with retainers according to the prior art. The resulting advantages are explained in detail above.

Figure 3:
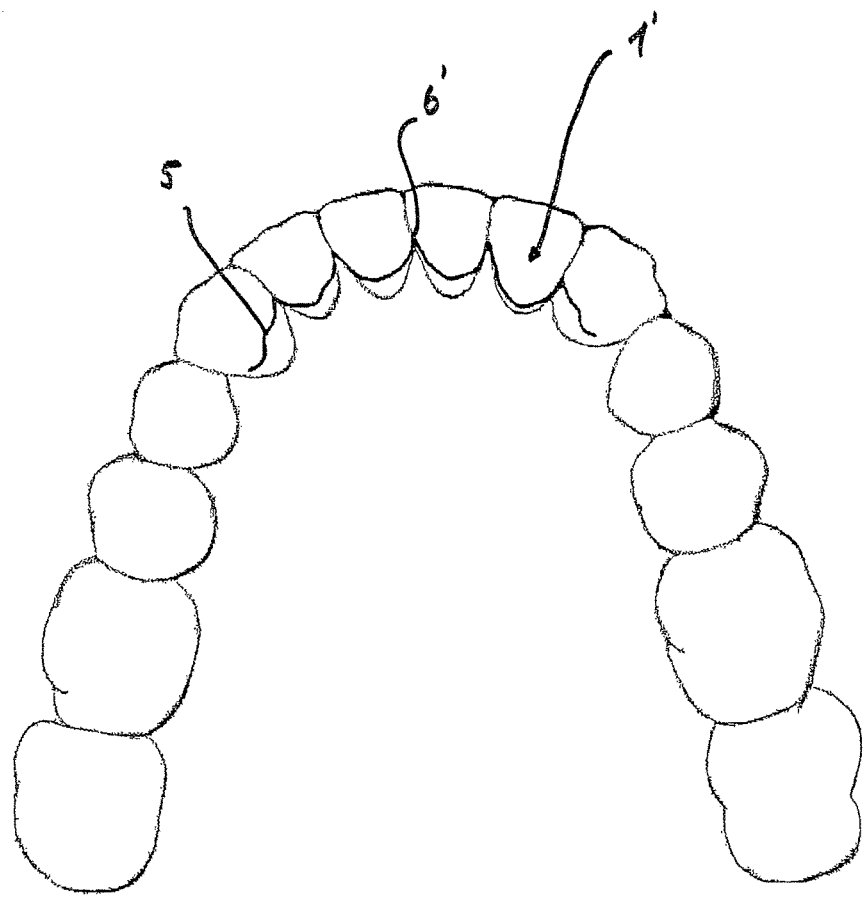
FIG. 3 is a sketch of a retainer used on a model of a lower jaw.

FIG. 3 shows another example of a retainer 1' according to the invention, wherein the retainer 1' is adapted for use in a lower jaw. The retainer 1' like the retainer 1 is connected to six teeth in a force-transmitting manner, however, the retainer is shown in FIG. 3 in its inserted state, i.e. without the junctions necessary for a connection. Here, tips 6' of the retainer 1' protrude into interdental spaces between the teeth such that shifting the retainer 1' relative to the teeth is blocked at least in a transverse direction. From the figure it is clear that the amplitude of the tips 6' are significantly larger in the retainer 1' than is the case in the retainer 1. This results from the natural shape of the teeth.

Figure 4:
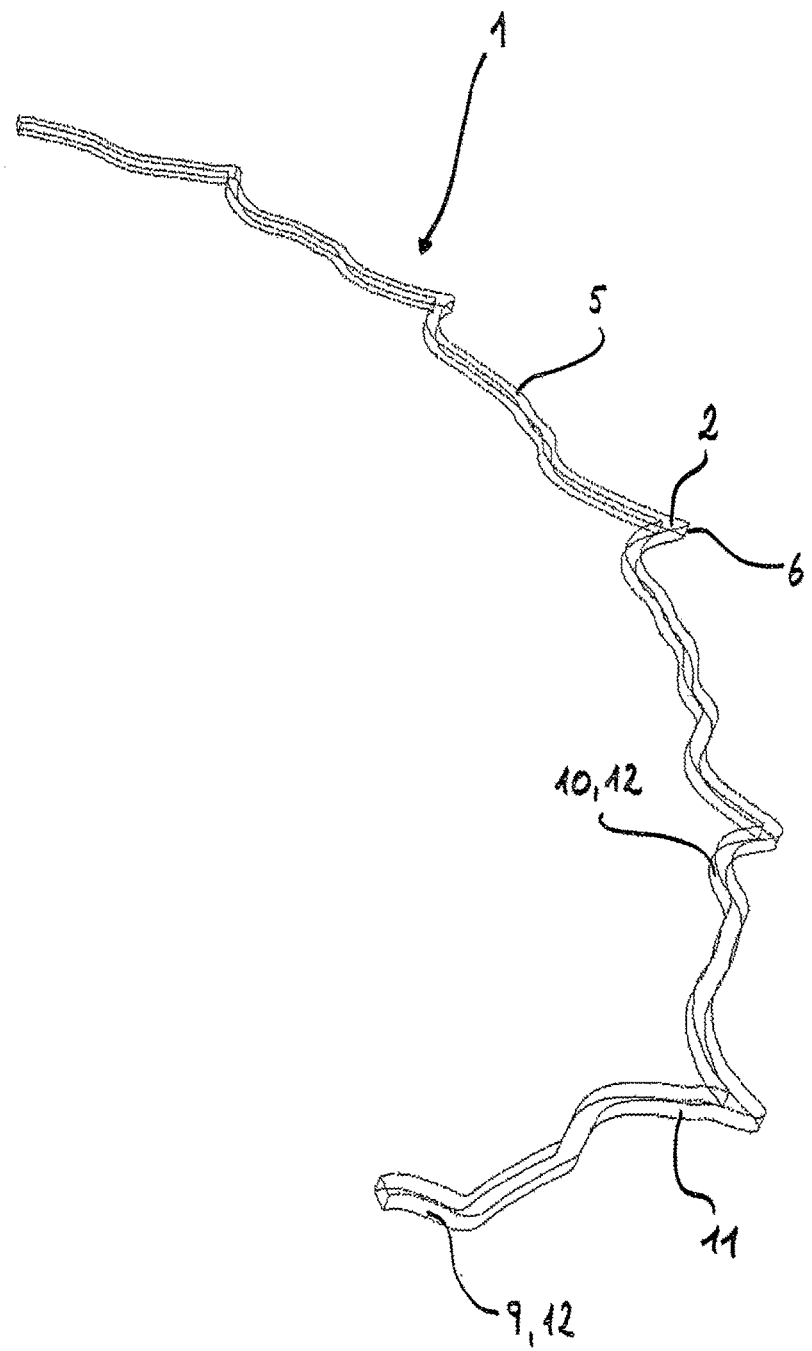
FIG. 4 is similar to FIG. 1, but is illustrated as a three-dimensional lattice model.

The retainer 1 is finally shown in FIG. 4 in a three-dimensional lattice model. From the illustration it is clear that the retainer 1 has a square cross-section, wherein a side length of the cross section is 0.3 mm. Likewise, in FIG. 4 both a front surface 9 and a rear surface 10 of the retainer 1 are shown. These are arranged parallel to one another, wherein the front surface 9 faces a tooth surface of the respective abutting tooth in an installed state of the retainer 1. Perpendicular to the front surface 9 and the rear surface 10 the upper surface 2 and a lower surface 11 of the retainer 1 are oriented.

The upper surface 2 and the lower surface 11 of the retainer 1 each extend in one plane. These planes define a metal sheet (not shown) from which the retainer 1 was originally machined, wherein the metal sheet has a thickness of 0.3 mm. This means that a machining tool (laser, water jet, erosion wire, etc.) has been traversed parallel to the upper surface 2 of the retainer 1 over the metal sheet corresponding to the contour of the retainer 1 in order to machine the retainer 1 from the metal sheet. By means of this process step the front surface 9 and the back surface 10 of the retainer 1 have been obtained. These are therefore to be understood as processing planes 12 or machining surfaces 13 because they represent the planes that have been processed or where the retainer 1 has been machined. After machining the retainer 1 is provided directly in the illustrated form and may be applied to the patient's teeth without further adaptations.

Figure 5:
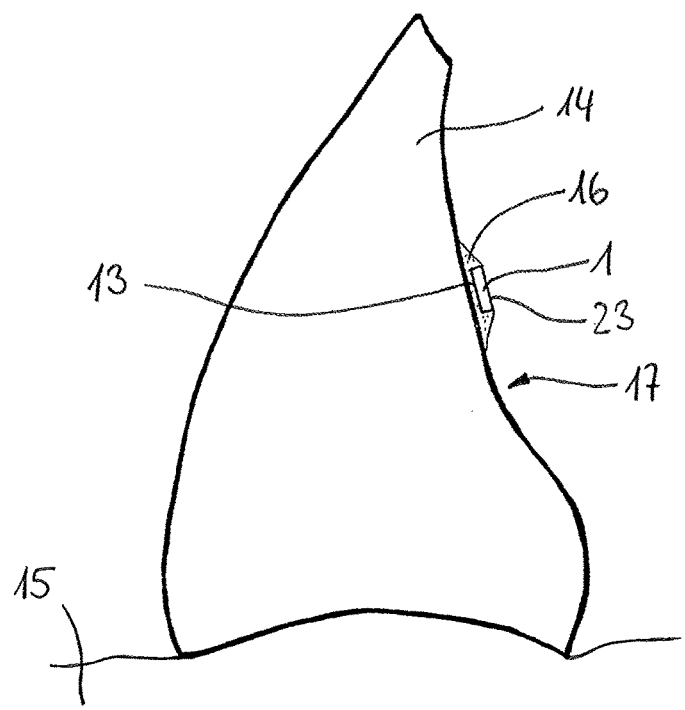
FIG. 5 is a cross section through a teeth provided with a retainer according to the invention.
Figure 6:
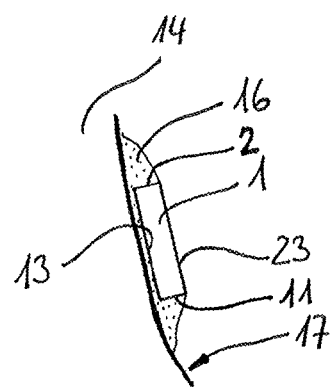
FIG. 6 is an enlarged view of the retainer of FIG. 5.

FIG. 5 shows a cross section through an incisor 14 which is provided with the retainer 1 according to the invention of FIG. 1, wherein only the area of the incisor 14 is shown, which is located above the gums 15. For the sake of clarity, FIG. 6 shows an enlarged view of the retainer 1 in FIG. 5. In a bonding portion—in which the retainer 1 is bonded with the incisor 14—the retainer 1 is embedded into a bonding material 16, which previously has been applied onto an inner tooth surface 17 and abuts quasi directly the tooth surface 17. The surface with which the retainer 1 abuts the tooth surface 17 corresponds to the machining surface 13 of the retainer 1, i.e. a cutting edge 18 which was formed during the production of the retainer 1. The upper surface 2 of the retainer 1 corresponds to an upper metal sheet surface 19 and the lower surface 11 of the retainer 1 corresponds to a lower metal sheet surface, wherein said upper and lower sheet surface 19 are parallel to each other. The upper and the lower sheet surface correspond to an original metal sheet plane. The upper surface 2 and the lower surface 11 of the retainer 1 extend perpendicular to the inner tooth surface 17.

Figure 6A:
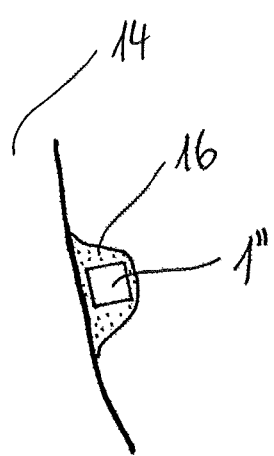
FIG. 6a is an enlarged view of an alternatively formed retainer.

FIG. 6a shows an alternative formed retainer 1'' which has a square cross section and is mounted in its bonding portion by means of the bonding material 16 at the incisor 14 such that it is completely surrounded by the bonding material 16.

Figure 7:
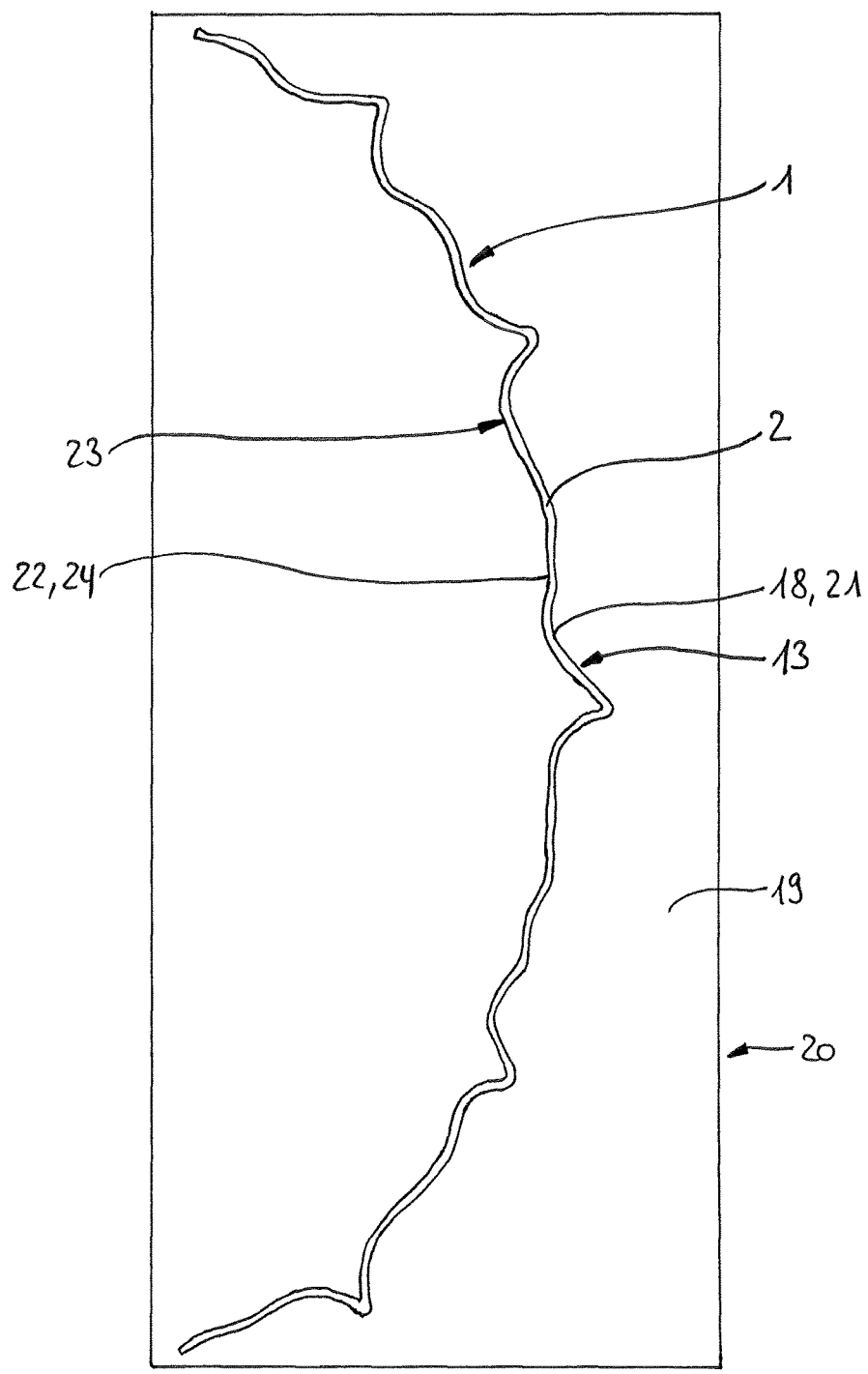
FIG. 7 is a plan view of a nitinol sheet with a worked out retainer.

Finally, FIG. 7 shows a plan view of a nitinol sheet 20, wherein the process of working out the retainer 1 according to the invention in FIG. 1 has just been completed and the finally cut out retainer 1 is still disposed within the nitinol sheet 20. The surface of the nitinol sheet 20 and the retainer 1 which extends in the drawing plane corresponds to the upper nitinol sheet surface 19 or the upper side 2 of the retainer 1. The cutting edge 18 of the retainer 1, of which only a line 21 is visible in the figure, extends perpendicular to the drawing plane. It corresponds to the machining surface 13 of the retainer 1, which comes to abut the inner tooth surface 17. A cutting edge 22 extending parallel to the cutting edge 18, which again is only visible as a line 24 in FIG. 7, is also to be regarded as a machining surface 23, which faces away from the inner tooth surface 17 in the inserted state.

REFERENCE NUMERALS AND DESIGNATIONS 1, 1', 1'' retainer
2 upper surface
3 arc
4 formation
5 wave
6, 6' tip
7 enveloping parabola
8 enveloping parabola
9 front surface
10 rear surface
11 lower surface
12 processing plane
13 machined surface
14 incisor
15 gums
16 bonding material
17 inner tooth surface
18 cutting edge
19 upper metal sheet surface
20 nitinol sheet
21 line
22 cutting edge
23 machined surface
24 line

What is claimed is:
1. A retainer adapted to cooperate with a plurality of teeth and configured to stabilize the plurality of teeth, the retainer comprising:
at least one elongated arc which is shaped overall to a natural curvature of a lower jaw or an upper jaw,
wherein the at least one elongated arc is locally adapted individually to a surface contour of respective abutting teeth,
wherein the retainer is machined from a sheet metal plate and includes two mutually parallel surfaces,
wherein the sheet metal plate is made from a nickel titanium alloy,
wherein the retainer contacts a tooth surface in an installed condition of the retainer,
wherein a machined surface of the retainer faces the tooth surface in the installed condition of the retainer,
wherein an upper side or a lower side of the retainer corresponds to an original surface plane of the sheet metal plate, and
wherein the retainer is locally formed so that it protrudes at least partially into an interdental space arranged between two adjacent teeth so that a relative movement between the retainer and the two adjacent teeth directed in a longitudinal direction of the retainer is blocked even when the retainer abuts at the two adjacent teeth in an unconnected state.
2. The retainer according to claim 1,
wherein the retainer is able to connect to the respective abutting teeth within bonding portions by a bonding material in a force-transferring manner,
wherein the retainer is embedded in the bonding material and is able to adhere to the respective abutting teeth,
wherein a position of the retainer is able to be positioned a minimum distance from a respective tooth surface measured perpendicular to the respective tooth surface, and wherein a maximum distance between the respective tooth surface and the position of the retainer, is able to be set at the most 0.1 mm in each of the bonding portions.

3. The retainer according to claim 1, wherein the arc has a local radius of curvature of 1.0 mm or less.

4. The retainer according to claim 1,
wherein the arc has a parallelogram-shaped or rectangular cross section, and
wherein side lengths of the cross section are at most 0.7 mm.

5. The retainer according to claim 1, wherein the retainer is able to connect to at least three teeth in a force-transferring manner.

6. The retainer according to claim 1, wherein the retainer is completely enclosed by a bonding material at the bonding portions.

7. The retainer according to claim 1, wherein the retainer is configured in one piece.

8. The retainer according to claim 1,
wherein the retainer viewed in plan view is enclosable by an inner enveloping parabola and an outer enveloping parabola, and
wherein when installed locally in a region of an interdental space a distance measured perpendicular to the inner enveloping parabola between the inner enveloping parabola and the outer enveloping parabola is at least 1.0 mm.

9. The retainer according to claim 1,
wherein the retainer has an at least partially roughened surface, and
wherein all surfaces extending in the longitudinal direction of the retainer are roughened.

10. The retainer according to claim 1, wherein a surface of the retainer is at least partially treated by electro-polishing or plasma polishing.

11. The retainer according to claim 1, wherein the nickel titanium alloy has an AF temperature between 25° C. and 35° C.

12. A method for producing a retainer comprising the steps:
detecting individual contours of teeth to be stabilized and generating a detected contour;
converting the detected contour of the teeth into a digital model and designing the retainer on the basis of the model;
machining the designed retainer from a metal sheet which is made from of a nickel titanium alloy, on the basis of the model using a computer-controlled process,
installing the retainer so that a machined surface of the retainer faces a tooth surface at which the retainer abuts,
wherein an upper side or a lower side of the retainer corresponds to an original surface plane of the sheet metal, and
wherein the retainer is locally formed so that it protrudes at least partially into an interdental space arranged between two adjacent teeth so that a relative movement between the retainer and the two adjacent teeth directed in a longitudinal direction of the retainer is blocked even when the retainer abuts at the two adjacent teeth in an unconnected state.

13. The method according to claim 12, wherein the retainer is cut out from the metal sheet by laser cutting or by wire erosion.

14. The method according to claim 12, wherein a contour of the teeth to be stabilized is detected intraorally.

15. The method according to claim 12,
wherein the metal sheet from which the retainer is machined is curved about at least one axis of curvature, and
wherein the at least one axis of curvature extends within a surface plane of the metal sheet.

16. The method according to claim 12, wherein the retainer after it has been machined from the metal sheet is electro-polished or plasma polished, so that edges of the retainer are rounded.

17. A retainer able to cooperate with a plurality of teeth and configured to stabilize the plurality of teeth, the retainer comprising:
at least one elongated arc which is shaped overall to a natural curvature of a lower jaw or an upper jaw,
wherein the at least one elongated arc is locally adapted individually to a surface contour of respective abutting teeth,
wherein the retainer is machined from a sheet metal plate and includes two mutually parallel surfaces,
wherein the retainer is able to connect to the respective abutting teeth within bonding portions by a bonding material in a force-transferring manner,
wherein the retainer is embedded in the bonding material and able to adhere to the respective abutting teeth,
wherein a maximum distance between a respective tooth surface and a position of the retainer is at the most 0.1 mm in each of the bonding portions, and
wherein the retainer is locally formed so that it protrudes at least partially into an interdental space arranged between two adjacent teeth so that a relative movement between the retainer and the two adjacent teeth directed in a longitudinal direction of the retainer is blocked even when the retainer abuts at the two adjacent teeth in an unconnected state.

18. A method for producing a retainer comprising the steps:
detecting individual contours of teeth to be stabilized and generating a detected contour;
converting the detected contour of the teeth into a digital model and designing the retainer on the basis of the model;
machining the designed retainer from a metal sheet which is made from of a nickel titanium alloy on the basis of the model using a computer-controlled process,
installing the retainer so that a machined surface of the retainer faces a tooth surface at which the retainer abuts,
wherein an upper side or a lower side of the retainer corresponds to an original surface plane of the sheet metal, and
wherein the retainer is locally formed so that it protrudes at least partially into an interdental space arranged between two adjacent teeth so that a relative movement between the retainer and the two adjacent teeth directed in a longitudinal direction of the retainer is blocked even when the retainer abuts at the two adjacent teeth in an unconnected state.

19. A method for producing a retainer cooperating with a plurality of teeth and configured to stabilize the plurality of teeth, the retainer comprising:
at least one elongated arc which is shaped overall to a natural curvature of a lower jaw or an upper jaw,
wherein the at least one elongated arc is locally adapted individually to a surface contour of respective abutting teeth, and wherein the retainer is machined from a sheet metal plate and includes two mutually parallel surfaces, the method comprising the steps of:

detecting individual contours of teeth to be stabilized and generating a detected contour;

converting the detected contour of the teeth into a digital model and designing the retainer on the basis of the model;

machining the designed retainer from a metal sheet which is made from of a nickel titanium alloy, on the basis of the model using a computer-controlled process; and installing the retainer so that a machined surface of the retainer faces a tooth surface at which the retainer abuts, wherein an upper side or a lower side of the retainer corresponds to an original surface plane of the sheet metal, and wherein the retainer is locally formed so that it protrudes at least partially into an interdental space arranged between two adjacent teeth so that a relative movement between the retainer and the two adjacent teeth directed in a longitudinal direction of the retainer is blocked even when the retainer abuts at the two adjacent teeth in an unconnected state.

* * * * *